(12) United States Patent
Ebata et al.

(10) Patent No.: US 8,729,176 B2
(45) Date of Patent: May 20, 2014

(54) POLYRICINOLEATE COMPOSITION AND PROCESS FOR PRODUCING THE SAME

(75) Inventors: Hiroki Ebata, Ichihara (JP); Shuichi Matsumura, Kanagawa (JP)

(73) Assignee: Keio University, Tokyo (JP)

( * ) Notice: Subject to any disclaimer, the term of this patent is extended or adjusted under 35 U.S.C. 154(b) by 744 days.

(21) Appl. No.: 12/310,731

(22) PCT Filed: Sep. 4, 2007

(86) PCT No.: PCT/JP2007/067225
§ 371 (c)(1),
(2), (4) Date: Mar. 5, 2009

(87) PCT Pub. No.: WO2008/029805
PCT Pub. Date: Mar. 13, 2008

(65) Prior Publication Data
US 2009/0270550 A1    Oct. 29, 2009

(30) Foreign Application Priority Data
Sep. 6, 2006   (JP) ................................. 2006-242027

(51) Int. Cl.
*C08L 33/02*   (2006.01)

(52) U.S. Cl.
USPC ........ 524/558; 524/559; 526/318.3; 528/26.5; 528/74.5; 528/111.5; 528/158.5; 528/245.5; 528/271; 528/272; 528/290

(58) Field of Classification Search
USPC ............... 524/558, 559; 526/318.3; 528/26.5, 528/74.5, 111.5, 158.5, 245.5, 272, 339.5
See application file for complete search history.

(56) References Cited

U.S. PATENT DOCUMENTS

| | | | |
|---|---|---|---|
| 2,787,601 A * | 4/1957 | Detrick et al. | 521/159 |
| 4,593,041 A | 6/1986 | Casley-Smith | |
| 5,858,934 A | 1/1999 | Wiggins et al. | |
| 6,277,902 B1 * | 8/2001 | Scholl | 523/213 |
| 7,169,860 B2 | 1/2007 | Bastioli et al. | |
| 7,196,124 B2 | 3/2007 | Parker et al. | |
| 7,196,157 B2 | 3/2007 | Bastioli et al. | |
| 7,253,250 B2 | 8/2007 | Farachi et al. | |
| 7,288,618 B2 | 10/2007 | Bastioli et al. | |
| 2004/0161464 A1 * | 8/2004 | Domb | 424/486 |
| 2004/0192859 A1 * | 9/2004 | Parker et al. | 525/438 |
| 2006/0165627 A1 * | 7/2006 | Allef et al. | 424/70.11 |
| 2007/0293591 A1 * | 12/2007 | Matsumura | 521/48 |

FOREIGN PATENT DOCUMENTS

| | | | |
|---|---|---|---|
| JP | 60-147224 | | 8/1985 |
| JP | 63-218750 | | 9/1988 |
| JP | 1-270932 | | 10/1989 |
| JP | 5-125166 | | 5/1993 |
| JP | 5-211878 | | 8/1993 |
| JP | 10-46180 | | 2/1998 |
| JP | 2002-539309 | | 11/2002 |
| JP | 2005-113001 | | 4/2005 |
| JP | 2005-523355 | | 8/2005 |
| JP | 2005-523356 | | 8/2005 |
| JP | 2005-523357 | | 8/2005 |
| JP | 2006-002145 | * | 1/2006 |
| JP | 2006-516998 | | 7/2006 |
| WO | WO 2005/105908 | * | 11/2005 |

OTHER PUBLICATIONS

Sperling et al Simultaneous interpenetrating networks based on castor oil elastomes and polystyrene: A review of an international program, ASC symposium series, Sep. 1980.*

Slivniak, Raia et al., "Macrolactones and Polyesters from Ricinoleic Acid", Biomacromolecules, 2005, vol. 6, No. 3, pp. 1679-1688.

Slivniak, Raia et al., "Lactic Acid and Ricinoleic Acid Based Copolyesters", Macromolecules, 2005, vol. 38, No. 13, pp. 5545-5553.

Krasko, et al. Poly(ester anhydride)s Prepared by the Insertion of Ricinoleic Acid into Poly(sebacic acid), Journal of Polymer Science, 2003, vol. 41, pp. 1059-1069.

Office Action in CN Appln No. 200780032680.3 dated Dec. 9, 2010.

* cited by examiner

*Primary Examiner* — Gregory Listvoyb
(74) *Attorney, Agent, or Firm* — Foley & Lardner LLP

(57) ABSTRACT

A process is disclosed wherein ricinoleic acid from petroleum alternative vegetable castor oil that has a hydroxyl group at the 12-position or a derivative thereof (an ester or a hydrogenated compound thereof) is polymerized in the presence of a synthetic zeolite and an immobilized lipase at around normal temperature without using any harmful polymerization catalysts or organic solvents which can cause environmental pollution whereby a polyester useful in the industry that has a weight average molecular weight of 20,000 or more is obtained. This high-molecular weight polyester is crosslinked to give a crosslinked elastomer that is comparable to synthetic rubbers.

12 Claims, 1 Drawing Sheet

Time course of polycondensation
of ricinoleic acid

POLYRICINOLEATE COMPOSITION AND PROCESS FOR PRODUCING THE SAME

TECHNICAL FIELD

The present invention relates to novel nonpetroleum ricinoleic acid polymers.

In detail, the invention relates to novel high-molecular weight polyricinoleates that are obtained from ricinoleic acid or a derivative thereof under catalysis of an immobilized lipid hydrolyzing enzyme (lipase).

In more detail, the invention relates to polyricinoleate compositions comprising a novel high-molecular weight polyricinoleate and a crosslinking agent, and polyester elastomers obtained by crosslinking the polyricinoleate compositions.

BACKGROUND OF THE INVENTION

The increasingly tense situation in the Middle East such as Iraq and Iran, and the development of industrial infrastructure in developing countries such as China have intensified the competition for petroleum resources as materials or energy sources and consequently oil prices have been increased worldwide. Research has been then actively carried out for the development of alternative energy to oil and materials based on naturally-occurring substances as alternatives to petroleum materials.

Meanwhile, the industry addresses global warming by reducing carbon dioxide emission in product manufacturing. Research has been then actively carried out for the development of energy-saving apparatuses or processes and the development of recycling materials such as biodegradable materials or reliably safe products against environmental pollution.

The research of recycling materials actively focuses on biodegradable polyesters, in particular aliphatic polyesters, and there are a number of patent applications directed to such polymers. For example, Patent Documents 1 to 3 disclose thermoplastic biodegradable aliphatic copolyesters that contain an aliphatic dicarboxylic acid or ester thereof, an aliphatic or cycloaliphatic diol, and an unsaturated acid of natural origin or ester thereof. Patent Document 4 discloses a method of synthesizing biodegradable aliphatic polyesters from one or more aliphatic dicarboxylic acids or esters thereof and one or more linear or branched aliphatic glycols under catalysis of monobutylstannoic acid.

Further, Patent Document 5 discloses a biodegradable vegetable oil grease that contains a natural base oil or a polymerized triglyceride; at least one of an alkyl phenol, a benzotriazole and an aromatic amine; and a metal based material wherein the metal is an alkali or alkaline earth metal.

For the synthesis of polyesters containing ricinoleic acid from fats, Non-Patent Document 1 reports that ricinoleic acid lactone and lactide are mixed in a predetermined ratio at high temperatures with a Sn or Z compound as a catalyst to give a copolymer having a molecular weight of 5,000 to 16,200 and a melting point of 100 to 130° C. The use of such copolymers in DDS is studied. It is reported that such copolymers have lower crystallinity than polylactic acid and are hydrolyzed more easily. Non-Patent Document 2 reports that a random copolymer with a molecular weight of 6,000 to 14,000 is obtained by polycondensing ricinoleic acid and lactic acid at high temperatures in a predetermined ratio and vacuum treating the resultant polyester. In these non-patent documents, the polyesters are synthesized by metal-catalyzed ring-opening polymerization via lactone or by polycondensation at high temperatures under reduced pressure. The molecular weight of the thus-obtained polyesters containing ricinoleic acid is low. Further, these non-patent documents do not report properties or performances of the copolymer polyesters with lactic acid.

Patent Document 6 discloses a polyester compound wherein the molecular structure is formed from a hydroxy fatty acid and an aliphatic dicarboxylic acid and has an amino group at a molecular end. Patent Document 7 discloses a reactive biodegradable copolymer for medical material use wherein the ricinoleic acid content is controlled by regulating the polycondensation reaction between ricinoleic acid and lactic acid. These materials, however, are obtained by methods similar to the polymerization for the polyesters described in Non-Patent Documents 1 and 2.

Patent Document 8 discloses a crosslinked ricinoleic acid composition elastomer that is formed from castor oil or a ricinoleic acid derivative, an epoxidized oil and a polycarboxylic acid in the presence of a peroxide initiator. A sheet material of the elastomer is described to show good mechanical strength and elasticity and be resistant to abrasion and hydrolysis.

Enzyme-catalyzed polymerization has been reported as a method for the production of biodegradable polyesters other than by thermal polycondensation. In detail, a lipase that is a hydrolyzing enzyme is used to facilitate esterification in the equilibrium reaction. According to this method, polyesters are synthesized from fats or fatty acids using an enzyme lipase that is immobilized for efficient use of the lipase.

In this respect, Patent Document 9 discloses a process wherein a polyester is produced from ricinoleic acid with use of a lipase immobilized on a calcined zeolite carrier while controlling the water content in the carrier at not more than 800 mg per 1 g of the immobilized enzyme.

In the production of polyesters from ricinoleic acid according to the known literature as described above, the enzyme reaction in the polymerization has a lower optimum temperature than thermochemical reactions to enable energy-saving and does not involve harmful organic solvents or catalysts. Accordingly, this polyester synthesis method is favorable in terms of global warming and environmental pollution. In Examples of Patent Document 9, however, the dehydration-condensation rate for estolides is followed based on the neutralization value and no estolides showing a neutralization value of 30 or less are obtained in Examples. From the neutralization values described therein, the average molecular weights of the polyesters are estimated to be less than 3,000, that is, the polyesters have a relatively low molecular weight.

Patent Document 1: JP-A-2005-523355
Patent Document 2: JP-A-2005-523356
Patent Document 3: JP-A-2005-523357
Patent Document 4: JP-A-2002-539309
Patent Document 5: JP-A-H10-46180
Patent Document 6: JP-A-H05-125166
Patent Document 7: JP-A-2005-113001
Patent Document 8: JP-A-2006-516998
Patent Document 9: JP-A-H05-211878
Non-Patent Document 1: Biomacromolecules 2005, 6, 1679-1688
Non-Patent Document 2: Macromolecules 2005, 38, 5545-5553

The literature described above has not reached a technical level at which biodegradable polyesters that are aimed at oil independence and do not contribute to global warming or environmental pollution may be produced by industrial processes with economic advantages.

In the field of rubber products, which is an expected application of the present invention, natural rubbers that are generally-used nonpetroleum materials mainly have a polyisoprene skeleton in which isoprene molecules are cis-1,4-bonded. However, they contain large amounts of high-molecular weight gels and proteins, and this fact makes quality stabilization difficult. In addition, they are poor in plasticity and processability as they are, and the processing thereof entails mastication (molecular scission) and addition of various antioxidants to increase durability.

Various synthetic rubbers have been developed as materials supplementing these defects of the natural rubbers. However, such synthetic rubbers are of oil origin and are generally not biodegradable. These petroleum synthetic rubbers are diene rubbers such as butadiene rubbers (BR), isoprene rubbers (IR), chloroprene rubbers (CR), rubbers of isobutene and a little isoprene (HR), styrene/butadiene rubbers (SBR) and butadiene/acrylonitrile rubbers (NNR); and non-diene rubbers such as ethylene/propylene rubbers (EPM), copolymers of ethylene, propylene and a little non-conjugated diene (EPDM), Hypalon from reaction of polyethylene with sulfur dioxide and chlorine, urethane rubbers from addition polymerization of diol and diisocyanate, polysulfide rubbers from polycondensation of dichloroethane and sodium tetrasulfide, silicone rubbers from ring-opening polymerization of cyclic siloxanes, and fluororubbers from copolymerization of vinylidene fluoride and trifluorochloroethylene.

These synthetic rubbers have excellent weather resistance, oil resistance, solvent resistance, chemical resistance, abrasion resistance and heat resistance and are used in tires, belts, automotive parts and other various industrial parts. Further, the synthetic rubbers are used in a wider range of applications as complex materials with other characteristic materials.

The use of these synthetic rubbers has spread to various industrial fields. However, stable supply of oil that is the material of these synthetic rubbers has been threatened. The fact that the synthetic rubbers are petroleum polymers makes it very difficult to recycle the materials, and disposing the materials causes environmental pollution. Furthermore, it is needless to say that eliminating or saving organic solvents or thermal energy in the polymerization for these synthetic rubbers is advantageous. The polymers obtained according to the present invention may be used as alternatives to the conventional rubber materials.

DISCLOSURE OF THE INVENTION

As described in connection with the background art above, polymer materials used in the industry are of oil origin, and elastomers containing such materials are widely used. Accordingly, there are a number of problems in terms of oil independence, environmental pollution and energy saving.

To solve these problems, polymers should be produced from oil alternatives such as natural materials in an efficient manner with a catalyst such as protein enzyme capable of catalyzing the polymerization at lower temperature than thermochemical reaction to achieve energy-saving, and without harmful materials such as toxic industrial catalysts.

The present inventors have found natural materials derived from for example vegetable oils that can be polymerized or crosslinked with a naturally-occurring catalyst such as enzyme capable of catalyzing the reaction efficiently at around room temperature without using any materials harmful to human, whereby oil independence, energy-saving and environmental pollution prevention can be achieved.

In detail, the inventors have found a process for synthesizing high-molecular weight polyesters useful in the industry wherein ricinoleic acid from castor oil that has a hydroxyl group on the number 12 carbon atom or a derivative thereof (an ester or a hydrogenated compound thereof) is polycondensed at around normal temperature with use of an enzyme lipase that is immobilized for effective use of the enzyme. By crosslinking the high-molecular weight polyesters, elastomers comparable to synthetic rubbers can be obtained.

Ricinoleic acid is an unsaturated hydroxy acid that is found in abundance in *Ricinus communis* oil and its chemical name is 12-hydroxy-cis-9-octadecenoic acid. The acid is represented by the formula below.

The present invention is very advantageous in that the ricinoleic acid is obtained inexpensively and is an environmentally friendly industrial material.

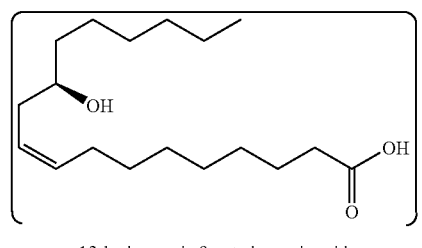

12-hydroxy-cis-9-octadecenoic acid

In the present invention, ricinoleic acid or a derivative thereof (an ester or a hydrogenated compound thereof) has a molecular weight of about 300. The ricinoleic acid or derivative thereof has a hydroxyl group at the 12-position in the molecule and a carboxyl group or a carboxylate group at an end of the molecule, whereby it undergoes esterification or ester exchange reaction and is self-condensed to form a linear polymer. This polymerization reaction is catalyzed by an immobilized lipase in the presence of a synthetic zeolite or is performed under azeotropic dehydration conditions at reduced pressure.

The present invention is summarized as follows.

(1) A polyricinoleate obtained by polymerizing ricinoleic acid or a derivative thereof under catalysis of an immobilized lipid hydrolyzing enzyme (lipase) and having a weight average molecular weight (Mw) of not less than 20,000.

(2) The polyricinoleate as described in (1), wherein a synthetic zeolite is used in the polymerization without actual contact.

(3) The polyricinoleate as described in (1) or (2), which has a glass transition temperature of not more than −40° C. as determined with a differential scanning calorimeter (DSC).

(4) A polyricinoleate composition comprising a polyricinoleate and a crosslinking agent wherein the polyricinoleate is obtained by copolymerizing ricinoleic acid or a derivative thereof and has a weight average molecular weight (Mw) of not less than 20,000.

(5) A crosslinked polyester elastomer obtained from the polyricinoleate composition described in (4).

(6) The polyester elastomer as described in (5), wherein the crosslinked polyester elastomer satisfies the following requirements (I) and (II) in a viscoelasticity test:

$$G^*(-30°\ C.)/G^*(20°\ C.) \leq 3.0 \quad (I)$$

$$G^*(-70°\ C.)/G^*(20°\ C.) \geq 10.0 \quad (II).$$

ADVANTAGES OF THE INVENTION

According to the present invention, ricinoleic acid or a derivative thereof (an ester or a hydrogenated compound thereof) obtained from castor oil that is a naturally-occurring inexpensive vegetable oil may be polymerized into a high-molecular weight polyricinoleate at relatively lower temperatures than by usual chemical reaction, under catalysis of an immobilized enzyme in combination with a synthetic zeolite without any harmful polymerization catalysts or organic solvents that can cause environmental pollution. The combined use of an immobilized enzyme and a synthetic zeolite enables more efficient production of the high-molecular weight polymers.

In the invention, the enzyme reaction is performed with good reaction efficiency at relatively low temperatures at which the immobilized enzyme can remain active. Consequently, the polyesters may be produced while energy-saving is achieved, and carbon dioxide emission is drastically reduced compared to thermal condensation reaction.

PREFERRED EMBODIMENTS OF THE INVENTION

According to the present invention, industrially valuable high-molecular weight polymers may be synthesized from nonpetroleum materials such as ricinoleic acid or derivatives thereof by enzyme reaction with excellent reaction efficiency without solvents at mild temperatures compared to usual chemical reactions. The elastomers of the invention are obtained from the polymers.

The ricinoleic acid derivatives include ricinoleates and hydrogenated ricinoleic acids such as 12-hydroxystearic acid.

The starting material ricinoleic acid or derivative thereof having a weight average molecular weight of about 300 is polymerized relatively easily by thermal polycondensation or by esterification or ester exchange reaction using a hydrolyzing enzyme lipase.

For the production of the desired elastomers, the molecular weight of polyesters from ricinoleic acid or derivatives thereof greatly affects mechanical strength or rubber elasticity. If the molecular weight is low, the elastomers will not be used as alternatives to the conventional elastomers or synthetic rubbers.

In the present invention, polyesters having a weight average molecular weight of 20,000 or more may be easily prepared by enzyme reaction while successively removing condensation water (in the case of ricinoleic acid) or lower alcohols (in the case of ricinoleates) from the reaction system. Such polyesters are useful as materials of elastomers.

The polyricinoleates obtained with an immobilized lipid hydrolyzing enzyme (lipase) as a catalyst have a weight average molecular weight (Mw) of 20,000 to 500,000, preferably 25,000 to 450,000, and more preferably 27,000 to 400,000.

In the invention, polyesters are synthesized from ricinoleic acid or derivatives thereof using a lipid hydrolyzing enzyme lipase capable of catalyzing condensation reaction at relatively low temperatures. Accordingly, the invention contributes to energy-saving, and the polyesters obtained in the invention are free of toxic catalysts and do not involve organic solvents required in usual chemical reactions.

Further, the immobilized enzyme can be used repeatedly to catalyze the condensation reaction and shows higher thermal stability than chemically unmodified enzymes. Accordingly, the enzyme reaction can be easily controlled in a stable manner and the enzyme will not remain in the polyesters and will not adversely affect properties of elastomers obtained from the polyesters. That is, polyesters of high purity may be easily obtained with less energy. The combined use of the immobilized enzyme with a synthetic zeolite enables more efficient production of high-molecular weight polymers.

The polyesters from ricinoleic acid or derivatives thereof obtained in the invention have a high weight average molecular weight. Such high-molecular weight polyesters will not be obtained by usual enzyme reaction.

Figure 1:
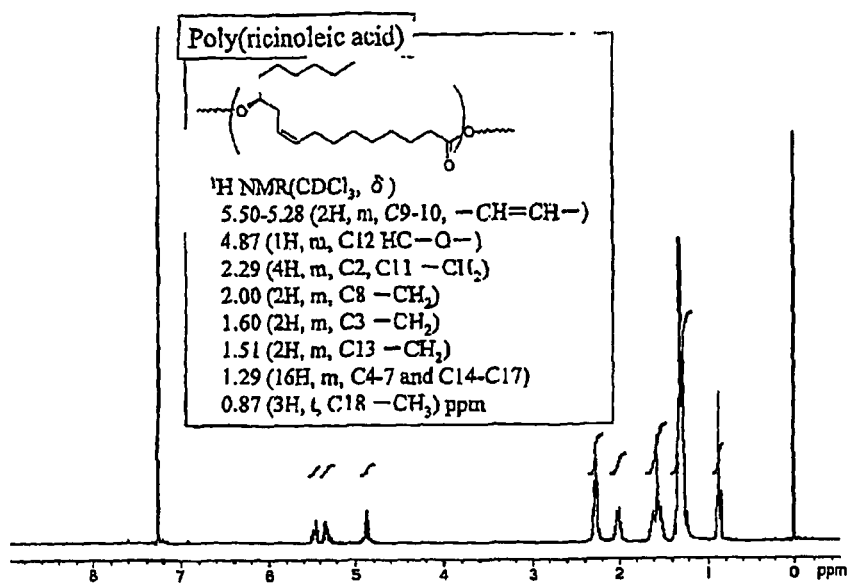
FIG. 1 is one of structure analysis diagrams of polymers according to the present invention.

FIG. 1 shows results of structure analysis.

In order to obtain the polymers of the invention, the ester polymerization of fatty acid or fatty acid ester under catalysis of the enzyme lipase which controls reversible reaction should be performed while successively removing water or lower alcohols through the controlling of the reaction system by for example maintaining the reaction system at reduced pressure. However, the use of synthetic zeolites such as molecular sieve 4A enables the ester polymerization to take place more simply and easily and also provides polyesters having a higher molecular weight.

The synthetic zeolites for use in the invention are inorganic porous substances having uniform fine pore diameters. Molecules that are smaller than the fine pore diameters are adsorbed in the fine pores, whilst molecules larger than the fine pore diameters cannot enter the fine pores and thus are not adsorbed therein, whereby these molecules are separated. That is, the synthetic zeolites function as molecular sieves. The structures of the synthetic zeolites are not particularly limited as long as the zeolites can separate water or lower alcohols generated during the polyester formation.

The following reaction formula shows an example of elastomer production wherein ricinoleic acid, methyl ricinoleate or ester ricinoleate as a starting material is synthesized into a polyester with an enzyme lipase and is then formed into an elastomer with a peroxide crosslinking agent.

By using the high-molecular weight polyricinoleates as starting materials, the present invention has made it possible for the first time to produce nonpetroleum elastomers as alternatives to the conventional petroleum polymeric resin elastomers.

[Chem. 1]

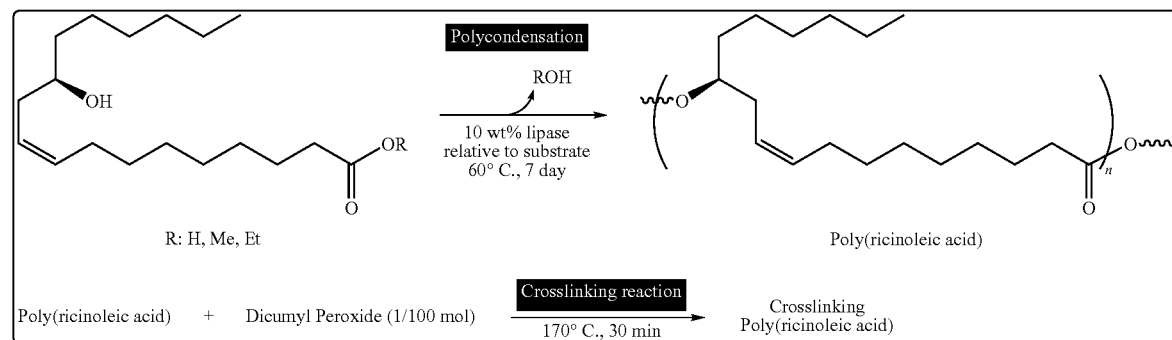

(Reaction Formula)

The enzymes for use in the invention may be commercially available various fungal lipases. A study by the present inventors has shown that excellent polyester polymerization results are obtained with lipase from *Burkholderia cepacia* and lipase from *Candida antarctica*.

However, the enzymes in the invention are not limited to these fungal lipases, and the invention may use any enzymes which have enzymatic activity and stability such that polyricinoleates having a weight average molecular weight of not less than 20,000 may be obtained on an industrial scale and which are inexpensive in view of these enzyme performances.

The enzymes may be immobilized by any methods. Exemplary methods include immobilization by adsorption on organic or inorganic carriers, immobilization by crosslinking the enzyme molecules whereby the enzyme is rendered insoluble in the polymerization system (crosslinking method), and immobilization by encapsulating the enzyme in polymeric gels such as alginic acid gels or polymer gels. The immobilization methods are not particularly limited as long as the methods are simple and the immobilized enzyme shows high activity and stability.

For the evaluation of appearance and properties of the polyesters obtained in the invention, DSC, stereomicroscopes, optical microscopes and rheometers are preferably used.

Effects of the use of synthetic zeolite (molecular sieve 4A) in the lipase-catalyzed polymerization of ricinoleic acid or derivatives thereof were tested.

Methyl ricinoleate or ethyl ricinoleate was used as a starting material, and the amount of catalyst lipase was changed. The temperature was 60° C. or 80° C. The yield was obtained in each test. In some tests, molecular sieve (MS 4A) was used in combination.

The polymerization results are shown in Table 1.

pounds. The sulfur compounds include sulfur, sulfur chloride, sulfur dichloride, morpholine disulfide, alkylphenol disulfide, tetramethylthiuram disulfide and selenium dithiocarbamate. Of the sulfur and sulfur compounds, sulfur is preferable and is desirably used in an amount of 0.1 to 10 parts by weight, preferably 0.3 to 5 parts by weight, and more preferably 0.3 to 3 parts by weight based on 100 parts by weight of the polyricinoleate.

The organic peroxides include dicumyl peroxide, 2,5-dimethyl-2,5-di(t-butylperoxy)hexane, 2,5-dimethyl-2,5-di(benzoylperoxy)hexane, 2,5-dimethyl-2,5-di(t-butylperoxy)hexyne-3, di-t-butyl peroxide, di-t-butylperoxy-3,3,5-trimethylcyclohexane and t-dibutyl hydroperoxide. Of these, dicumyl peroxide, di-t-butyl peroxide and di-t-butylperoxy-3,3,5-trimethylcyclohexane are preferable.

The organic peroxides are generally used in amounts of 0.001 to 0.05 mol, preferably 0.002 to 0.02 mol, and more preferably 0.005 to 0.015 mol based on 100 g of the polyricinoleate.

When the sulfur compounds are used as the vulcanizing agents, vulcanization accelerators are preferably used together. Examples of the vulcanization accelerators include thiazole compounds such as N-cyclohexyl-2-benzothiazole sulphenamide, N-oxydiethylene-2-benzothiazole sulphenamide, N,N'-diisopropyl-2-benzothiazole sulphenamide, 2-mercaptobenzothiazole, 2-(2,4-dinitrophenyl)mercaptobenzothiazole, 2-(2,6-diethyl-4-morpholinothio)benzothiazole and dibenzothiazyl disulfide; guanidine compounds such as diphenylguanidine, triphenylguanidine and diorthotolylguanidine; aldehyde amine compounds such as acetaldehyde-aniline condensate and butylaldehyde-aniline condensate; imidazoline compounds such as 2-mercaptoimidazoline; thiourea compounds such as diethylthiourea and dibutylthiourea; thiuram compounds such as tetramethylthiuram monosulfide and tetramethylthiuram dis-

TABLE 1

|  |  | Test Ex. 1 | Test Ex. 2 | Test Ex. 3 | Test Ex. 5 | Test Ex. 4 | Test Ex. 6 |
|---|---|---|---|---|---|---|---|
| [Materials] (1) |  |  |  |  |  |  |  |
| Ricinoleic acid | mg | 100 | 100 |  |  |  |  |
| Methyl ricinoleate | mg |  |  | 100 | 100 | 100 | 100 |
| [Catalyst] (2) |  |  |  |  |  |  |  |
| Lipase | wt % | 50 | 50 | 50 | 50 | 50 | (3) 50 |
| [Polymerization conditions] |  |  |  |  |  |  |  |
| Temperature | ° C. | 80 | 80 | 60 | 60 | 80 | 80 |
| MS 4A (present or absent) |  | Absent | Present | Absent | Present | Absent | Present |
| [Results] |  |  |  |  |  |  |  |
| Yield | wt % | 89.6 | 86.8 | 95.6 | 90.1 | 94.5 | 91.4 |
| Weight average molecular weight (Mw) | g/mol | 6,900 | 7,900 | 1,740 | 76,890 | 2,080 | 69,000 |

(1) Manufactured by SIGMA-ALDRICH
(2) Lipase manufactured by Amano Enzyme Inc. (immobilized enzyme derived from *Bulkholderia cepacia*)
(3) Novozym 435 manufactured by Novozym Japan Ltd. (immobilized enzyme derived from *Candida antarctica*)

[Vulcanizing Agents, Vulcanization Accelerators, Vulcanization Auxiliaries]

The high-molecular weight polyricinoleates may be used as they are. When they are used in the form of crosslinked elastomers, the high-molecular weight polyricinoleates are crosslinked with sulfur or peroxides. The elastomers thus obtained show excellent elastomeric properties that are not achieved by polyricinoleates of low molecular weight.

In detail, compounds capable of forming a vulcanized system such as vulcanizing agents, vulcanization accelerators and vulcanization auxiliaries are added to the polymers. Examples of the vulcanizing agents include sulfur compounds, organic peroxides, phenolic resins and oxime comulfide; dithioic acid salts such as zinc dimethyldithiocarbamate, zinc diethyldithiocarbamate and tellurium diethyldithiocarbamate; xanthate compounds such as zinc dibutylxanthate; and others such as zinc oxide.

The vulcanization accelerators are generally used in amounts of 0.1 to 20 parts by weight, preferably 0.2 to 15 parts by weight, and more preferably 0.5 to 10 parts by weight based on 100 parts by weight of the polyricinoleate.

When the organic peroxides are used as the vulcanizing agents, vulcanization auxiliaries are preferably used together. Examples of the vulcanization auxiliaries include sulfur; quinone dioximes such as p-quinone dioxime; acrylic compounds such as ethylene glycol dimethacrylate and trimethylolpropane trimethacrylate; allyl compounds such as diallyl phthalate and triallyl isocyanurate; maleimide compounds; and divinyl benzene. The vulcanization auxiliaries are generally used in amounts of 0.5 to 2 mol, preferably 0.5 to 1.5 mol, and more preferably an approximately equimolar amount per 1 mol of the organic peroxides.

Activators may be used as required in the invention. Examples thereof include glycols such as polyethylene glycol and diethylene glycol; and amines such as di-n-butylamine and triethanolamine. The activators are generally used in amounts of 0.2 to 10 parts by weight, preferably 0.3 to 5 parts by weight, and more preferably 0.5 to 4 parts by weight based on 100 parts by weight of the polyricinoleate.

Other additives generally added to rubbers such as reinforcing agents, fillers, anti-aging agents and processing aids may be used appropriately while still achieving the object of the invention.

[Reinforcing Agents and Inorganic Fillers]

It is preferable to use reinforcing agents to improve mechanical properties such as tensile strength, tear strength and abrasion resistance of the high-molecular weight polyricinoleates. Specific examples include carbon blacks such as SRF, GPF, FEF, MAF, HAF, ISAF, SAF, FT and MT; these carbon blacks surface-treated with silane coupling agents or the like; silica, activated calcium carbonate, fine powdery talc and fine powdery silicic acid. Inorganic fillers such as light calcium carbonate, heavy calcium carbonate, talc and clay may be used.

These additives may be used at 10 to 300 parts by weight, preferably 30 to 250 parts by weight, and more preferably 30 to 230 parts by weight based on 100 parts by weight of the polymer.

[Anti-Aging Agents]

A single or two or more anti-aging agents may be used in the invention. The amount of the anti-aging agents is desirably 0.1 to 10 parts by weight, preferably 0.2 to 8 parts by weight, and more preferably 0.5 to 5 parts by weight based on 100 parts by weight of the polyricinoleate.

Similar to usual rubber compositions, the product life may be extended by using the anti-aging agents. Conventional anti-aging agents such as amine anti-aging agents, phenol anti-aging agents and sulfur anti-aging agents may be used.

Specific examples of the anti-aging agents include aromatic secondary amine anti-aging agents such as phenylbutylamine and N,N-di-2-naphthyl-p-phenylenediamine; phenol anti-aging agents such as dibutylhydroxytoluene and tetrakis[methylene(3,5-di-t-butyl-4-hydroxy) hydrocinnamato]methane; thioether anti-aging agents such as bis[2-methyl-4-(3-n-alkylthiopropionyloxy)-5-t-butylphenyl]sulfide; dithiocarbamate anti-aging agents such as nickel dibutyldithiocarbamate; zinc salts of 2-mercaptobenzoylimidazole and 2-mercaptobenzoimidazole; and sulfur anti-aging agents such as dilauryl thiodipropionate and distearyl thiodipropionate.

[Processing Aids]

Processing aids generally used in rubbers may be used for the polymer compositions according to the present invention. Specific examples include stearic acid, palmitic acid, lauric acid, barium stearate, zinc stearate, calcium stearate and esters of these acids. The processing aids may be appropriately used at not more than 10 parts by weight, preferably not more than 8 parts by weight, and more preferably not more than 6 parts by weight based on 100 parts by weight of the polyricinoleate.

[Preparation of Polyricinoleate Composition]

According to the method A2 in JIS K 6395-5.2, the polyricinoleate was kneaded with the specified amounts of additives (e.g., carbon black, stearic acid, zinc oxide) or crosslinking agents and crosslinking auxiliaries to give a polyricinoleate composition.

[Preparation of Crosslinked Elastomer]

A crosslinked elastomer was obtained by crosslinking the polyricinoleate composition by hot pressing at 170° C. for 30 minutes according to JIS K 6299.

[Measurement of Vulcanized Rubber Properties]

(1) Measurement of HA (Hardness)

The hardness was tested by measuring the spring hardness (JIS A hardness) in accordance with JIS K 6253.

(2) Tensile Test

According to JIS K 6251-3, the tensile strength and elongation of the crosslinked elastomer were measured by testing dumbbell specimen by the method specified in JIS K 6251 at a measurement temperature of 25° C. and a tensile rate of 50 mm/min.

(5) Viscoelasticity Test

The pressed sheet of crosslinked elastomer prepared in the preparation of crosslinked elastomer was punched out to a size of 10 mm wide×40 mm long×2 mm thick, and was tested with a viscoelastometer. In detail, the dynamic shear modulus G' (dyn/cm$^2$) and dynamic shear loss G" (dyn/cm$^2$) were determined with dynamic viscoelastometer ARES (manufactured by Rheometric Scientific Inc.) at measurement temperatures of −70 to 80° C., a frequency of 10 Hz and a strain of 1%. The complex dynamic elastic modulus G* and complex dynamic viscosity E* were obtained from the following equations:

$$G^* = G' + iG' \quad E^* = E' + iE'$$

$$\tan \delta = G''/G'$$

The present invention will be described in greater detail based on examples hereinbelow.

Example 1

The molecular weights of polyricinoleates obtained by enzyme reaction were studied. The substrates were ricinoleic acid, methyl ricinoleate and ethyl ricinoleate (all manufactured by SIGMA-ALDRICH). The substrate was reacted under catalysis of 50 wt % immobilized lipase (derived from *Burkholderia cepacia*, manufactured by Amano Enzyme Inc.) based on weight of the substrate at 80° C. for 168 hours in the presence or absence of molecular sieve 4A (MS 4A).

The weight average molecular weights of the polyesters formed are shown in Table 2.

TABLE 2

| Sample No. | Substrate | MS 4A | Weight average molecular weight | Yield (%) |
|---|---|---|---|---|
| 1 | Ricinoleic acid | Absent | 6,900 | 89.6 |
| 2 | Ricinoleic acid | Present | 7,900 | 86.8 |
| 3 | Methyl ricinoleate | Absent | 2,080 | 94.5 |
| 4 | Methyl ricinoleate | Present | 73,200 | 89.8 |
| 5 | Ethyl ricinoleate | Absent | 2,710 | 96.5 |
| 6 | Ethyl ricinoleate | Present | 58,620 | 88.5 |

In the above polyester forming reactions, the presence of the molecular sieve 4A did not affect the molecular weights of the polyesters when the substrate was ricinoleic acid. In contrast, the presence of the molecular sieve 4A greatly affected the molecular weights of the polyesters in the case of the ricinoleates and it was demonstrated that the use of MS 4A drastically increased the molecular weights. Although the use of MS 4A resulted in slightly lower yields, it was still advantageous in the industry in view of the high molecular weight.

Example 2

Methyl ricinoleate (manufactured by SIGMA-ALDRICH) was polymerized under catalysis of 50 wt % immobilized lipase (manufactured by Amano Enzyme Inc.) based on weight of the ester at 60° C., 80° C. or 100° C. in the presence or absence of molecular sieve 4A (MS 4A) in the reaction system. The molecular weights of the polyesters are compared in Table 3.

TABLE 3

| Sample No. | Reaction temperature (° C.) | MS 4A | Weight average molecular weight | Yield (%) |
|---|---|---|---|---|
| 7 | 60 | Absent | 1,740 | 95.6 |
| 8 | 60 | Present | 76,890 | 90.1 |
| 3 | 80 | Absent | 2,080 | 94.5 |
| 4 | 80 | Present | 73,200 | 89.8 |
| 9 | 100 | Absent | 2,460 | 96.1 |
| 10 | 100 | Present | 63,040 | 87.1 |

As shown in Table 3, the reactions at a low temperature of 60° C. where the thermal stability of the immobilized lipase was easily maintained resulted in contrary results depending on the presence or absence of molecular sieve 4A. In detail, the reaction without the molecular sieve afforded a polyester having a weight average molecular weight far below 3,000; in contrast, the molecular weight of the polyester was increased to above 70,000 by the use of the molecular sieve. The results showed a tendency that the weight average molecular weight was decreased with increasing reaction temperature.

Example 3

Methyl ricinoleate as an enzyme reaction substrate was polymerized in the presence of molecular sieve 4A at a reaction temperature of 80° C. in the same manner as in Example 2 except that the amount of the immobilized lipase based on weight of the substrate was 10%, 50% or 100%. Changes in molecular weight of the polyesters obtained were studied.

The results are shown in Table 4.

TABLE 4

| Sample No. | Immobilized lipase amount (%) | Weight average molecular weight | Yield (%) |
|---|---|---|---|
| 11 | 10 | 21,500 | 88.8 |
| 12 | 50 | 73,200 | 89.8 |
| 13 | 100 | 92,700 | 86.9 |

Example 4

Figure 2:
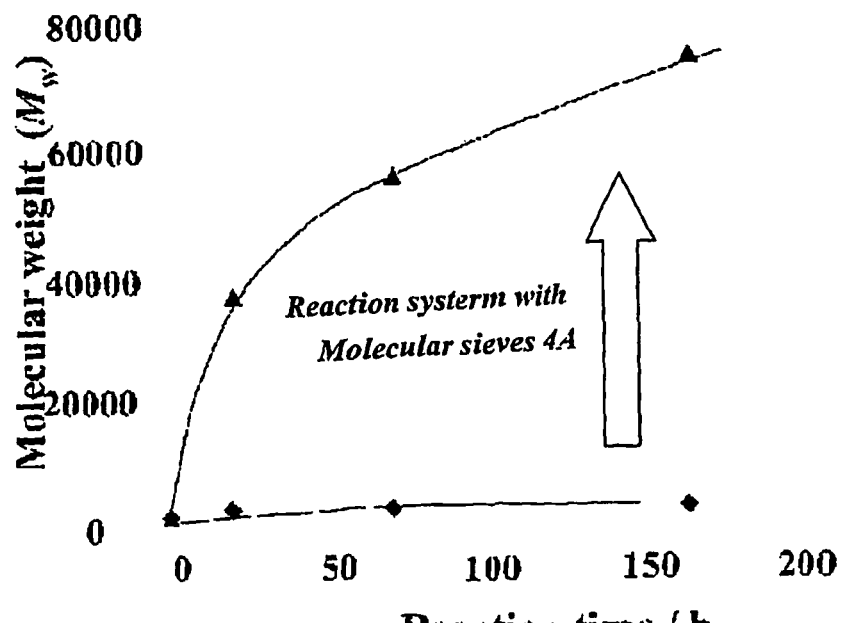
FIG. 2 is one of views plotting weight average molecular weights against reaction time of polyesters obtained by condensation catalyzed by an immobilized lipase in the presence of molecular sieve 4A.

The enzyme reaction was performed at 80° C. in the same manner as in Example 2 for various reaction times, and changes in molecular weight depending on the enzyme reaction time were studied. The results are shown in FIG. 2. The reaction in the presence of the molecular sieve 4A for 100 hours (about 4 days) afforded a polyester having a weight average molecular weight of about 60,000, and the reaction for 168 hours produced a high-molecular weight polyester having a weight average molecular weight of over 70,000.

Example 5

The polyester from Sample No. 13 in Example 3 that had a weight average molecular weight of 92,700 was tested on a differential scanning calorimeter (DSC) to determine the glass transition temperature. The glass transition temperature was −60° C., and the polyester was found to be a liquid polymer showing no melting point or crystallization temperature.

Example 6

100 Parts by weight of the polyester from Sample No. 13 in Example 3 that had a weight average molecular weight of 92,700 was mixed with 1/100 mol concentration of dicumyl peroxide and was reacted therewith at 170° C. for 30 minutes. The polyester was quickly crosslinked and cured to give a flexible crosslinked elastomer.

The elastomer had a JIS A hardness of 50. A viscoelasticity test resulted in $G^*(-30°\ C.)/G^*(20°\ C.)=1.4$ and $G^*(-70°\ C.)/G^*(20°\ C.)=277.9$.

Example 7

100 Parts by weight of the polyester with a weight average molecular weight of 92,700 similar to Example 6 was mixed with 40 parts of carbon black SRF and 1/100 mol concentration of dicumyl peroxide and was reacted therewith at 170° C. for 30 minutes. The polyester was quickly crosslinked and cured to give a flexible crosslinked elastomer.

The elastomer had a JIS A hardness of 70, a 50% modulus of 2.23 MPa, a breaking strength of 2.95 MPa, and an elongation at break of 100%.

A viscoelasticity test resulted in $G^*(-30°\ C.)/G^*(20°\ C.)=1.2$ and $G^*(-70°\ C.)/G^*(20°\ C.)=49.0$.

100 Parts by weight of the polyester with a weight average molecular weight of 92,700 similar to Example 6 was mixed with 40 parts by weight of carbon black SRF, 5 parts by weight of two kinds of zinc oxides, 0.5 part by weight of Sanceler M, 1 part by weight of Sanceler TT and 1.5 parts by weight of sulfur, and was reacted therewith at 170° C. for 30 minutes. The polyester was crosslinked and cured to give a flexible crosslinked elastomer.

The elastomer had a JIS A hardness of 55, a 100% modulus of 0.9 MPa, a breaking strength of 1.88 MPa, and an elongation at break of 220%. A viscoelasticity test resulted in $G^*(-30°\ C.)/G^*(20°\ C.)=1.4$ and $G^*(-70°\ C.)/G^*(20°\ C.)=122.2$.

The invention claimed is:

1. A polyricinoleic acid polymer composition comprising a polyricinoleic acid polymer and a crosslinking agent, wherein the polymer has a weight average molecular weight (Mw) of not less than 21,500, is synthesized from at least one selected from a group consisting of ricinoleic acid and derivatives thereof, which is obtained by condensing at least one selected from a group consisting of ricinoleic acid and derivatives thereof and having a glass transition temperature of not more than −40° C. as determined with a differential scanning calorimeter (DSC).

2. The polyricinoleic acid polymer composition according to claim 1, wherein the crosslinking agent is a sulfur compound.

3. The polyricinoleic acid polymer composition according to claim 1, further comprising a reinforcing agent.

4. The polyricinoleic acid polymer composition according to claim 2, further comprising a reinforcing agent.

5. The polyricinoleic acid polymer composition according to claim 3, wherein the reinforcing agent is carbon black.

6. The polyricinoleic acid polymer composition according to claim 4, wherein the reinforcing agent is carbon black.

7. The polyricinoleic acid polymer composition according to claim 1, further comprising a vulcanization accelerator.

8. The polyricinoleic acid polymer composition according to claim 6, further comprising a vulcanization accelerator.

9. The polyricinoleic acid polymer composition according to claim 1, wherein the polymer is obtained by condensing at least one selected from a group consisting of ricinoleic acid and derivatives thereof under catalysis of an immobilized lipid hydrolyzing enzyme (lipase).

10. The polyricinoleic acid polymer composition according to claim 9, wherein in the condensing a synthetic zeolite is used without actual contact.

11. The polyricinoleic acid polymer composition according to claim 1, wherein the polymer has a weight average molecular weight of not less than 73,200.

12. The polyricinoleic acid polymer composition according to claim 7, wherein the polymer has a weight average molecular weight of not less than 73,200.

* * * * *